United States Patent [19]

Betts

[11] Patent Number: 5,525,331

[45] Date of Patent: Jun. 11, 1996

[54] INHIBITORS OF ESTERASE-PRODUCING MICRO-ORGANISMS, FOR USE PRIMARILY IN DEODORANT COMPOSITIONS

[75] Inventor: John A. Betts, Haslemere, United Kingdom

[73] Assignee: Robertet S.A., Grasse, France

[21] Appl. No.: 380,340

[22] Filed: Jan. 30, 1995

Related U.S. Application Data

[63] Continuation of Ser. No. 966,605, Oct. 26, 1992, abandoned, which is a continuation of Ser. No. 271,856, Nov. 10, 1988, abandoned, filed as PCT/GB87/00323, May 12, 1987, published as WO87/06827.

[30] Foreign Application Priority Data

May 13, 1986 [GB] United Kingdom .................. 8611650

[51] Int. Cl.$^6$ ..................................................... A61K 7/32
[52] U.S. Cl. ........................................................... 424/065
[58] Field of Search ................................................ 424/65

[56] References Cited

U.S. PATENT DOCUMENTS

| | | | |
|---|---|---|---|
| 3,808,319 | 4/1974 | Kanfoush et al. | 424/308 |
| 4,136,165 | 1/1979 | Moller et al. | 424/60 |
| 4,199,576 | 4/1980 | Reller et al. | 514/886 |
| 4,493,823 | 1/1985 | Moller et al. | 424/70 |
| 4,847,069 | 7/1989 | Bissett et al. | 424/59 |

FOREIGN PATENT DOCUMENTS

| | | | |
|---|---|---|---|
| 458964 | 6/1945 | Belgium | 514/938 |
| 0039857 | 5/1981 | European Pat. Off. | 514/859 |
| 2390160 | 12/1978 | France | 424/59 |
| 1583219 | 1/1981 | United Kingdom | 514/886 |

OTHER PUBLICATIONS

Pharmaceutical Formulas, 1947, vol. II, pp. 101, 102, 150–152, 165–168, 173, 302–315, 898–900, 379, 385, 386, 389, 391, 393 to 397, 405, 407 and 392.

*Primary Examiner*—Shelley A. Dodson
*Attorney, Agent, or Firm*—James Creighton Wray

[57] ABSTRACT

Inhibitors of esterase-producing micro-organisms, primarily for use in dermatology and cosmetics and with particular application to personal deodorants and to anti-fungal agents and other preparations for the treatment of acne, dandruff and tinea pedis. The active ingredient of the inhibitor comprises an aromatic acid ester of a phenol or of an aromatic alcohol, the phenol or aromatic alcohol being sufficiently water-soluble to impart an anti-microbial action and the aromatic acid being sufficiently water-soluble to impart an anti-microbial action and/or to lower the pH of liquid body-secretions to a level which at least inhibits the growth of micro-organisms in the liquid body-secretions.

31 Claims, No Drawings

INHIBITORS OF ESTERASE-PRODUCING MICRO-ORGANISMS, FOR USE PRIMARILY IN DEODORANT COMPOSITIONS

This application is a continuation of application Ser. No. 07/966,605 filed Oct. 26, 1992, now abandoned, which is a continuation of Ser. No. 07/271,856 filed Nov. 10, 1988, now abandoned.

This invention relates to inhibitors of esterase-producing micro-organisms for use primarily in deodorant compositions.

The human skin as a large natural population of micro-organisms. These organisms are nourished by various skin secreted substances, skin cell debris, breakdown products of the skin and the organisms themselves. The skin secretions are conveniently divided into two groups, water- and lipid-soluble materials; these are eccrine and apocrine sweat and sebum which will be referred to as 'liquid body-secretions' and will now be described, as will their functions as are generally understood.

Eccrine sweat consists mainly of a watery solution of dissolved salts and is produced by glands distributed over the whole skin surfaces. In conditions of occulsion, e.g. feet enclosed in socks and shoes, the eccrine sweat accumulates and in these warm, damp conditions, the skin debris, together with nutrients from the sweat, provide a medium for micro-organism growth with the possibility of massive overgrowth of one type. This can result, in the first instance, in odorous metabolic products, and in the second, in clinical infection with maceration of the skin and irritation.

Apocrine sweat is produced by the apocrine glands at specific sites on the body, notably the axillae, the angenital area and around the nipples. Although present at birth, the apocrine glands are not functional until puberty when they are influenced by circulating androgens. Apocrine secretion differs from eccrine sweat in containing lipids (fatty materials) and proteins. In the warm, damp occlusion met in the axilla, certain skin micro-organism metabolise this secretion, forming free fatty acids and other breakdown products. These materials are odorous and responsible for 'body odour'.

The sebaceous glands are distributed over the skin surface except the palms and dorsae. They are most numerous on the scalp, forehead, face, back and chest. The secretion, sebum, consists mainly of fatty materials, wax esters, cholesterol and its esters and squalene. Normally, sebum flows freely from the glands, spreading over the skin surface. In acneic and certain other skin conditions, the sebaceous duct through which the sebum is normally secreted becomes hyperkeratinised and the opening of the duct becomes blocked. The gland continues to produce sebum and the blocked duct distends to form a comedone. Also blocked in the duct, (the normally) commensal micro-organisms produce esterases which hydrolyse the sebum lipids, liberating free fatty acids. These fatty acids are irritant and can result in an inflammatory reaction along the wall of the duct. Leucocytes invade the inflamed area and the comedone develops into papule and then a pustule. This is a typical acne 'spot'.

The scalp is well supplied with sebaceous glands, and the scalp, like all skin, undergoes desquamation. Due to the presence of hair, the squames tend to be retained at the scalp surface. Sebum accumulates beneath these squames and in dandrufff conditions is hydrolysed by micro-organism produced esterases to form irritant fatty acids. The irritation causes proliferation of the epidermis and increased formation of the stratum corneum which again desquamates unevenly in large clumps—the dandruff scale or flake.

It is an object of the present invention to provide effective inhibitors of esterase-producing micro-organisms, and also preparations incorporating such inhibitors for use in deodorant compositions; one specific object is to provide a personal deodorant having a formulation which produces effective action over a substantial period of time, which is safe in application, and which is economical and safe to produce.

According to a principal aspect of the present invention, there is provided a deodorant composition comprising an inhibitor of esterase-producing micro-organisms in which the active ingredient comprises an aromatic acid ester of a phenol or of an aromatic alcohol, the phenol or aromatic alcohol being sufficiently water-soluble to impart an anti-microbial action and the aromatic acid being sufficiently water-soluble to impart an anti-microbial action and/or to lower the pH of liquid body-secretion to a level which at least inhibits the growth of micro-organisms in the liquid body-secretions, and the active ingredient being incorporated in a perfume composition which is then incorporated in a vehicle.

The invention also provides a compound when used in a deodorant composition to inhibit esterase producing micro-organisms, comprising an aromatic acid ester of a phenol or of an aromatic alcohol, the phenol or aromatic alcohol being sufficiently water-soluble to impart an anti-microbial action and the aromatic acid being sufficiently water-soluble to impart an antimicrobial action and/or to lower the pH of liquid bodysecretion to a level at least inhibits the growth of micro-organism in the liquid body-secretions.

The effect of the active ingredient is produced by the aforementioned microbial enzymes acting to split the constituents of the ester and so hydrolyse the ester back into the aromatic acid and the phenol or aromatic alcohol. On a skin surface, such as in deodorant applications, this action occurs almost immediately but, where skin penetration is involved, as in most dermatological applications, the action is progressive.

The above term 'anti-microbial action' means an action which inhibits microbial growth, rather than one which eliminates microbial growth completely as can be achieved by a microbicide. In such skin-surface and skin-penetrating applications, the esterases produced by the micro-organism hydrolyse a portion of the active ingredient and, in so doing, inhibit the action of the esterase and further growth of the micro-organism. After a period of time, the micro-organism may resume its metabolic activity and the above-mentioned process is repeated, and repetition will occur until the active ingredient is used us.

'Phenols' are, generally, aromatic compounds containing one or more hydroxyl groups directly attached to a benzene nucleus, but the phenols of the present invention may be restricted to those in which the other positions available on the benzene nucleus are occupied by hydrogen, hydroxyl, aliphatic, benzenoid or heterocyclic groups. Examples of such phenols useful in the present invention include phenol, cresols, xylenols, thymol, carvacrol, eugenol and isoeugenol.

'Aromatic alcohols' are, generally, aromatic compounds with a hydroxy group in a side chain attached to a benzene nucleus. Again, for the present invention, it is preferable that the other positions available on the benzene nucleus are occupied by hydrogen, hydroxyl, aliphatic, benzenoid or heterocyclic groups. Suitable examples include benzyl alcohol, phenylethyl alcohol, cinnamic alcohol and anisic alcohol.

'Aromatic acids' are, generally, compounds containing one or more carboxylic groups which are directly attached to a benzene nucleus or occur in a side chain. Yet again, it is preferable that the other positions available on the benzene nucleus are occupied by hydrogen hydroxyl, aliphatic, benzenoid or heterocyclic groups. Suitable examples include benzoic acid, salicyclic acid, cinnamic acid, phenyl-acetic and anisic acid.

The inhibitor according to the invention incorporates a microbial-inhibiting agent as opposed to the more usual triclosan bactericide which acts to eliminates rather than control the relevant microflora. Known microbicides and bactericides are usually powerful, and it is believed that the complete elimination of microflora, specifically cutaneous flora, is medically undesirable.

Embodiments of the present invention will now be described, by way of example.

As a deodorant for use in an aerosol spray or mechanical spray container, about 5% to 50% and preferably 20% of active ingredient of the invention is incorporated in a perfume composition, and about 1% of the perfume composition is added to a 96% ethanol excipient. The perfume composition of the invention will frequently be sold to an end-producer who will add the composition to his chosen vehicle.

As a dermatological agent in the form of a skin lotion, for the treatment of acne, between 0.5% and 20% and preferably about 5% of active ingredient is incorporated in a vehicle which may be composed of dimethyl sulphoxide, polyol, ethanol and water in suitable proportions. Anti-inflammatory substances such as hydrocortisone or glycyrrhetic acid and healing agents such as allantoin, may also be incorporated in the end product.

As a scalp lotion for the treatment of dandruff, active ingredient within the above percentages is incorporated in a hydro-alcoholic vehicle, using solubilising agents as necessary.

As a powder for the treatment of tinea pedia and foot odour, active ingredient (if liquid), within the above percentages, is absorbed onto amorphous silica powder or light magnesium carbonate which is then mixed with say 50% talcum, starch or other suitable powder. If the active ingredient is solid, usually crystalline, the crystals are finely ground, for example in a microniser, and then mixed with say 50% talcum, starch or other suitable powder.

Suitable perfume compositions may also be incorporated in the scalp/skin lotions and foot powders.

The skin and scalp lotions may be supplied in sprinkler bottles for application to the scalp or the affected skin area in the form of liquid droplets which are massaged into the scalp/skin. Alternatively, the lotion may be applied by means of a pad or compress which is pre-impregnated and supplied in a sealed package; the pad is partially exposed and then applied to an affected skin area, at least once per day. In further alternative forms, the inhibitors for use in treating the scalp or skin may comprise ointments, gels, creams, lotions, sprays or powders.

The inhibitors for foot treatment are preferably in powder form, as indicated above, but might also be supplied as liquids or in sprays etc.

I claim:

1. A deodorant composition for inhibiting esterase-producing micro-organisms comprising an active ingredient, a perfume composition that incorporates a percentage of the active ingredient, and a vehicle for carrying the perfume composition and the active ingredient, wherein the active ingredient is an aromatic acid ester of a phenol, wherein the phenol is sufficiently water-soluble to impart anti-microbial action, and wherein the aromatic acid is sufficiently water-soluble to impart, when dissolved in a liquid human body-secretion, an anti-microbial action and to lower the pH of the liquid body-secretion to a level which inhibits growth of micro-organisms in the liquid body-secretions.

2. A deodorant composition as claimed in claim 1, wherein said phenol is selected from the group consisting of phenol, cresols, xylenols, thymol, carvacrol, eugenol and isoeugenol, and wherein said aromatic acid is selected from the group consisting of benzoic acid, salicylic acid, cinnamic acid, phenyl-acetic acid and anisic acid.

3. A composition as claimed in claim 1, wherein said active ingredient comprises phenol ester or aromatic alcohol ester.

4. A composition as claimed in claim 1, wherein 5%–50% of said active ingredient is incorporated in said perfume composition and approximately 1% of the perfume composition is added to an approximately 96% ethanol excipient.

5. A composition as claimed in claim 1, wherein said vehicle comprises an alcohol.

6. A composition as claimed in claim 1, wherein said active ingredient is incorporated in a vehicle which comprises aqueous alcohol and/or skin penetrants to produce also a dermatological action.

7. A composition as claimed in claim 6, and further incorporating anti-inflammatory substances.

8. The composition of claim 6, further incorporating healing agents.

9. The composition of claim 7, further incorporating healing agents.

10. The deodorant composition of claim 1, wherein the vehicle is ethanol.

11. The deodorant composition of claim 1, wherein the vehicle has a skin penetrant selected from the group consisting of polyol and dimethyl sulfoxide.

12. The deodorant composition of claim 1, wherein the vehicle is a mixture of dimethyl sulphoxide, polyol, ethanol and water.

13. The deodorant composition of claim 12, wherein between 0.5% to 20% of the active ingredient is incorporated into the vehicle.

14. The deodorant composition of claim 1, further comprising anti-inflammatory substances selected from the group consisting of hydrocortisone and glycyrrhetic acid.

15. The deodorant composition of claim 1, further comprising healing agents such as allantoin.

16. The deodorant composition of claim 1, wherein the vehicle is a hydro-alcoholic vehicle, and further comprising solubilising agents.

17. The deodorant composition of claim 1, wherein the composition is in a form selected from the group consisting of ointments, gels, creams, lotions, sprays and powders.

18. The deodorant composition of claim 1, wherein the vehicle is a powder.

19. The deodorant composition of claim 18, wherein the powder is selected from the group consisting of amorphous silica powder and light magnesium carbonate.

20. The deodorant composition of claim 1, wherein the vehicle is a mixture of light magnesium carbonate and powder selected from the group consisting of starch and talcum.

21. A composition for topical application to skin which inhibits esterase-producing micro-organisms to provide a deodorant effect, comprising:

(a) a predetermined amount of an aromatic ester of a phenol, the phenol being sufficiently water-soluble to import an anti-microbial action and the aromatic acid being sufficiently water-soluble to import an anti-microbial action and to lower pH of liquid body-secretions to a level which at least inhibits growth of micro-organisms in the liquid body-secretions; and (a) a pharmaceutically-acceptable carrier.

22. A method for inhibiting the growth of esterase-producing micro-organisms on a skin surface of a human body comprising the step of applying to said skin surface a liquid composition containing a growth-inhibiting amount of an ester of (a) an aromatic acid and (b) a phenol, whereby esterase produced by the micro-organisms partially hydrolyses the ester into its acid and phenol components which are sufficiently soluble in liquid secretions located of the skin surface to inhibit further growth of the micro-organisms for a period of time by imparting an anti-microbial action and lowering pH of the liquid body-secretions, after which repeated hydrolysis and inhibition takes place until all of the ester is used up.

23. The method according to claim 22, wherein the phenol is selected from the group consisting of phenol, cresols, xylenols, thymol, carvacrol, eugenol and isoeugenol and the acid is selected from the group consisting of benzoic acid, salicylic acid, cinnamic acid, phenylacetic acid and anisic acid.

24. The method of claim 22, wherein applying the inhibiting composition further comprises incorporating an active ingredient in a vehicle.

25. The method of claim 24, wherein applying the inhibiting composition further comprises incorporating the active ingredient in a perfume composition and incorporating the perfume composition in the vehicle.

26. The method of claim 22, wherein applying the inhibiting composition further comprises spraying the composition on the skin surface.

27. The method of claim 22, wherein applying the inhibiting composition further comprises introducing droplets of the composition on the skin surface and massaging the composition in the skin surface.

28. The method of claim 22, further comprising pre-impregnating a pad with the inhibiting composition, and wherein applying the inhibiting composition further comprises contacting the skin surface with the pad.

29. The method of claim 22, wherein applying the inhibiting composition further comprises adsorbing an active ingredient on an amorphous silica powder and mixing the active ingredient and amorphous silica powder with 50% powder selected from a group consisting of talc and starch.

30. The method of claim 22, wherein applying the inhibiting composition further comprises adsorbing an active ingredient on light magnesium carbonate and mixing the active ingredient and light magnesium carbonate with 50% powder selected from a group consisting of talc and starch.

31. The method of claim 22, wherein applying the inhibiting composition further comprises grinding an active ingredient and mixing a ground active ingredient with a powder.

\* \* \* \* \*